United States Patent [19]

Mészáros et al.

[11] Patent Number: 4,495,189

[45] Date of Patent: * Jan. 22, 1985

[54] CONDENSED PYRIMIDINES

[75] Inventors: Zoltán Mészáros; József Knoll; Peter Szentmiklosi; Istvan Hermecz; Ágnes Horváth; Sándor Virág; Lelle Vasvári; Ágoston Dávid, all of Budapest, Hungary

[73] Assignee: Chinoin Gyogyszer es Vegyeszeti Termekek Gyara R.T., Budapest, Hungary

[*] Notice: The portion of the term of this patent subsequent to Jul. 17, 2001 has been disclaimed.

[21] Appl. No.: 364,753

[22] Filed: Apr. 2, 1982

Related U.S. Application Data

[63] Continuation-in-part of Ser. No. 14,689, Feb. 23, 1979, Pat. No. 4,472,398, which is a continuation-in-part of Ser. No. 742,464, Nov. 17, 1976, Pat. No. 4,460,771.

[30] Foreign Application Priority Data

Nov. 27, 1975 [HU] Hungary .............................. CI-1623

[51] Int. Cl.³ .................. A61K 31/505; C07D 471/04
[52] U.S. Cl. ..................................... 514/258; 544/282
[58] Field of Search ........................ 544/282; 424/251

[56] References Cited

U.S. PATENT DOCUMENTS

| 3,585,198 | 6/1971 | Meszaros et al. | 544/282 |
|---|---|---|---|
| 3,642,797 | 2/1972 | Lesher | 544/282 |
| 3,960,863 | 6/1976 | Sato et al. | 424/251 |
| 4,022,897 | 5/1977 | Yale et al. | 424/251 |
| 4,066,766 | 1/1978 | Kadin | 424/251 |
| 4,122,274 | 10/1978 | Juby | 544/282 |
| 4,192,944 | 3/1980 | Juby | 544/282 |
| 4,209,622 | 6/1980 | Mészáros et al. | 544/282 |

Primary Examiner—Glennon H. Hollrah
Assistant Examiner—James H. Turnipseed
Attorney, Agent, or Firm—Karl F. Ross; Herbert Dubno

[57] ABSTRACT

New compounds of the following formula are disclosed:

1,6-dimethyl-3-carbamoyl-4-oxo-1,6,7,8-tetrahydro-4H-pyrido(1,2-a)-pyrimidine;
1,6-dimethyl-3-(N-tertiary-butyl-carbamoyl)-4-oxo-1,6,7,8-tetrahydro-4H-pyrido(1,2-a)pyrimidine;
1,6-dimethyl-3-(N-2-phenethyl-carbamoyl)-4-oxo-1,6,7,8-tetrahydro-4H-pyrido(1,2-a)pyrimidine;
1,6-dimethyl-3-[N-(3,3-diphenyl-propyl)-carbamoyl]-4-oxo-1,6,7,8-tetrahydro-4H-pyrido(1,2-a)pyrimidine;
1,6-dimethyl-3-(N-phenyl-carbamoyl)-4-oxo-1,6,7,8-tetrahydro-4H-pyrido(1,2-a)pyrimidine; and
1,6-dimethyl-3-(N-methyl-carbamoyl)-4-oxo-1,6,7,8-tetrahydro-4H-pyrido(1,2-a)pyrimidine, as well as pharmaceutical compositions containing these compounds and a method of inhibiting thrombocyte aggregation in mammals employing a pharmaceutically effective amount of at least one of these compounds.

2 Claims, No Drawings

CONDENSED PYRIMIDINES

CROSS REFERENCE TO RELATED APPLICATIONS

This application is a continuation-in-part of Ser. No. 014,689 filed Feb. 23, 1979, now U.S. Pat. No. 4,472,398 which is a continuation-in-part of Ser. No. 742,464 filed Nov. 17, 1976, now U.S. Pat. No. 4,460,771.

The invention relates to new racemic or optically active pyrimido(1,2a)heterocyclic compounds of the formula

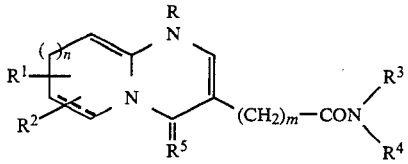

wherein
m is 0, 1 or 2;
n is 0, 1 or 2;
R is alkyl containing one to six carbon atoms;
$R^1$ is hydrogen or alkyl containing one to six carbon atoms;
$R^2$ is hydrogen, alkyl containing one to six carbon atoms; substituted or unsubstituted amino, substituted or unsubstituted hydroxy, carboxy or a group derived from a carboxylic acid or
$R^1$ and $R^2$ together form a —(CH=CH)$_2$—group attached to the two adjacent carbon atoms of the respective ring and the broken line represents a chemical bond;
$R^3$ is hydrogen, substituted or unsubstituted alkyl, substituted or unsubstituted aryl, substituted or unsubstituted aralkyl, substituted or unsubstituted heterocyclic moiety, substituted or unsubstituted cycloalkyl, substituted or unsubstituted acyl or substituted or unsubstituted hydroxy;
$R^4$ is hydrogen, substituted or unsubstituted alkyl, substituted or unsubstituted aryl, substituted and unsubstituted aralkyl, substituted or unsubstituted heterocyclic moieties, substituted or unsubstituted cycloalkyl, substituted or unsubstituted acyl or
$R^3$ and $R^4$ together with the nitrogen can form a substituted or unsubstituted five-, six- or seven-membered ring, which can contain a further heteroatom or heteroatoms;
$R^5$ is oxygen or a substituted or unsubstituted imino.

The invention further relates to new pharmaceutical compositions and to a new method of inhibiting thrombocyte aggregation. The new pharmaceutical compositions and method of treatment employ a pharmaceutically effective amount of the compounds of the formula (I).

The following compounds of the Formula (I) are especially effective in the inhibition of thrombocyte aggregation:
1,6-dimethyl-3-carbamoyl-4-oxo-1,6,7,8-tetrahydro-4H-pyrido-[1,2-a]pyrimidine;
1,6-dimethyl-3-(N-tertiary-butyl-carbamoyl)-4-oxo-1,6,7,8-tetrahydro-4H-pyrido[1,2-a]pyrimidine;
1,6-dimethyl-3-(N-2-phenethyl-carbamoyl)-4-oxo-1,6,7,8-tetrahydro-4H-pyrido[1,2-a]pyrimidine;
1,6-dimethyl-3-[N-(3,3-diphenyl-propyl)-carbamoyl]-4-oxo-1,6,7,8-tetrahydro-4H-pyrido[1,2-a]pyrimidine;
1,6-dimethyl-3-(N-phenyl-carbamoyl)-4-oxo-1,6,7,8-tetrahydro-4H-pyrido[1,2-a]pyrimidine; and
1,6-dimethyl-3-(N-methyl-carbamoyl)-4-oxo-1,6,7,8-tetrahydro-4H-pyrido[1,2-a]pyrimidine.

The new compounds are prepared:
(a) directly from the optionally racemic or optically active pyrimido(1,2a)heterocyclic quaternary compound of the formula

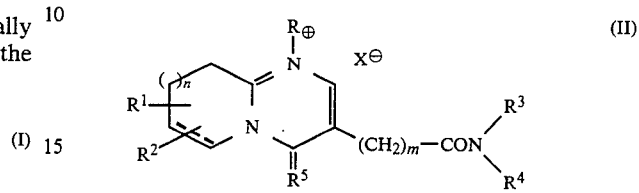

wherein m, n, R, $R^1$, $R^2$, $R^3$, $R^4$, $R^5$ and the dotted line are as defined above, and
X is an anion by reacting the compound of the formula II with an inorganic base, a salt thereof or with an organic base in the presence of an aprotic solvent or without any solvent, or
(b) from the optionally racemic or optically active pyrimido(1,2a)heterocyclic quaternary compound of the formula II in a protic solvent through the pyrimido(1,2a)heterocycle of the formula (III)

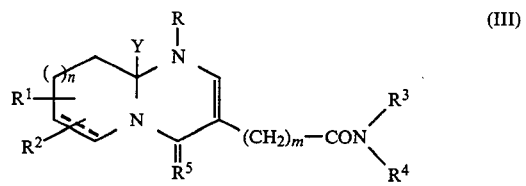

wherein m, n, R, $R^1$, $R^2$, $R^3$, $R^4$, $R^5$ and the dotted line are as defined above, Y is hydroxy, alkoxy, nitrile or substituted or unsubstituted amino, formed by reacting the compound of the formula II with an organic base or an inorganic base or a salt of the inorganic base, by splitting off HY from the molecule of the formula III or
(c) by reacting the racemic or optically active pyrimido(1,2a)heterocycle of the formula IV

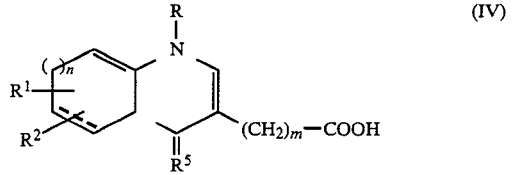

wherein m, n, R, $R^1$, $R^2$ and $R^5$ and the dotted line are as defined above, with an optically active amine of the formula V

wherein $R^3$ and $R^4$ are as defined above.

The method (a) is preferably carried out at 0°–200° C.

As aprotic solvents, aromatic hydrocarbons, preferably benzene; halogenated hydrocarbons, preferably chlorobenzene, chloroform, carbon tetrachloride; aliphatic ketones, preferably acetone and methyl ethyl ketone; ethers, preferably diethylether, dioxane; esters, preferably ethyl formate, ethylacetate or mixtures of the above solvents may be employed.

As an organic base trialkylamines, preferably triethylamine, trimethylamine, tributylamine; and nitrogen-containing aromatic heterocyclic compounds, such as pyridine may be used. If desired, an excess of the organic base may serve as an aprotic solvent.

As a salt of an inorganic base, alkali metal hydrogen carbonates, preferably sodium or potassium bicarbonate; alkali metal carbonates, preferably sodium or potassium carbonate; a salt of an alkali metal with an organic acid such as sodium or potassium acetate; or alkaline earth metal carbonates, preferably calcium carbonate, may be used.

The method (b) is preferably performed at temperatures of 0°–20° C.

As protic solvents, water; alcohols such as ethanol, n-propanol, isopropanol, n-butanol, glycol; or a mixture of said solvents can be employed.

Mixtures of the solvents enumerated for both methods (a) and (b) may also be used as the solvent.

As organic bases trialkyl-, dialkyl-, alkylamines, preferably triethylamine, diethylamine, n-butylamine; tetraalkylammoniumhydroxide, preferably tetraethylammoniumhydroxide; and nitrogen-containing heterocyclic compounds, such as pyridine or piperidine may be employed.

As inorganic bases alkali metal hydroxides, preferably sodium hydroxide, potassium hydroxide; alkali metal carbonates, preferably sodium carbonate, potassium carbonate; alkali metal bicarbonates preferably sodium bicarbonate, potassium bicarbonate; alkaline earth metal hydroxides, such as calcium hydroxide; alkaline earth metal carbonates, such as calcium carbonate; alkali metal cyanides; ammonium carbonate; ammonium bicarbonate or gaseous ammonia may be used.

Working according to methods (a) and (b), either the compound of the formula I is precipitated from the reaction mixture and removed by filtration, or it may be dissolved in a solvent and after evaporation the residue is recrystallized from a suitable solvent and the compound of the formula I is thus obtained.

According to one of the embodiments of method (c) a compound of the formula IV is reacted with an amine of the formula V by dissolving the compound of the formula IV in an organic solvent, preferably in chlorinated hydrocarbons, particularly in chloroform, or in ethers, such as dioxane, tetrahydrofurane, and a trialkyl amine preferably triethylamine or tributylamine is added. Thereafter an acid halide, preferably trimethyl acetic acid, such as trimethyl acetic acid chloride, or a chloroformic acid ester, preferably chloroformic acid methyl, ethyl or isopropylester is added dropwise to the obtained solution at −30° C. to 50° C., preferably at −20° C. to 0° C. The amine of the formula V is then added dropwise, if desired, dissolved in the above solvent or when using the acid addition salt thereof it is added together with the trialkylamine, such as triethylamine or tributylamine. The reaction mixture is then stirred at the above temperature range and then the mixture is shaken out with an aqueous solution of sodium bicarbonate and then with water whereafter it is allowed to warm to room temperature.

The reaction mixture is evaporated after drying and the residue is recrystallized from a suitable solvent.

According to another feature of method (c) a compound of the formula IV is reacted with an amine of the formula V, preferably in an organic solvent in the presence of a water-binding agent. Preferred water-binding agents are, for example, carbodiimides such as dicyclohexyl-carbodiimide. In such cases the reaction is preferably carried out in the presence of 1-hydroxy-benzotriazole, N-hydroxy-succinic imide or pentachlorophenol, as the presence of these substances minimizes the side reactions.

As solvents, aromatic hydrocarbons, such as benzene; chlorinated hydrocarbons, such as chloroform; chlorobenzene; ketones, such as acetone, methylethylketone; ethers, such as dioxane, tetrahydrofurane; esters such as ethyl acetate are preferred or when using a carbodiimide which is soluble in aqueous alcohol, a mixture of water and alcohol or a mixture of the said solvents can be employed.

The reaction is carried out at a temperature of 20° to 100° C. After the reaction is complete, the precipitated urea is removed by filtration and the residue obtained after the evaporation of the filtrate is recrystallized from a suitable solvent and thus the pyrimido(1,2a)-heterocycle of the formula I is obtained.

The pyrimido(1,2a)heterocyclic compounds of formulae II and IV can be prepared according to Hungarian Patent Specification Nos. 156,119, 158,085, 162,384, 162,373, 166,577 and Dutch Patent Specification No. 7,212,286.

The amines of the formula V are available.

The invention also includes the racemic and optically active forms of the pyrimido(1,2a)heterocyclic compounds of the formula I. Such are only possible, if at least one of $R^1$ and $R^2$ is different from hydrogen and $R^1$ and $R^2$ together do not form a —(CH=CH)$_2$-chain. The optically active compounds of the formula I may be obtained by resolving the racemic compounds of the formula I by methods known in the art, or the optically active forms of starting materials of the formulae II and IV are used.

The term "alkyl" means an alkyl group of one to six carbon atoms. The term "substituted amino" means an acylamino, preferably acetylamino, alkylamino, such as methylamino, ethylamino; dialkylamino, preferably dimethylamino or diethylamino group. The term "substituted hydroxy" indicates an alkoxy group, such as methoxy, ethoxy; aralkoxy such as benzyloxy group. The term "substituted alkyl group" means a straight or branched chain alkyl of one to six atoms, optionally bearing a substituted or unsubstituted amino, hydroxy, or substituted hydroxy, keto aryl or substituted aryl, carboxy or a group derived form a carboxylic acid. The term "aryl group" as used herein means phenyl or naphthyl groups; substituted aryl indicates only substituted amino, alkyl of one to six carbon atoms, hydroxy or substituted hydroxy, carboxy or a group derived from carboxylic acid or nitro groups. In the term "substituted aralkyl group" as used herein the "alk" means preferably alkyl of one to six carbon atoms, hydroxy or substituted hydroxy, amino or substituted amino, nitro, carboxy groups or a group derived form a carboxylic acid.

The term "heterocyclic group" means five-, six-, or seven-membered partially or completely saturated mono- and bicyclic heterocycles, containing nitrogen, oxygen sulphur atoms or nitrogen and oxygen; "substituted heterocycles" refer to such heterocycles substituted by alkyl, acyl or alkoxy of one to six carbon atoms. The term "cycloalkyl group" means a five-, sixor seven-membered cycloalkyl group; substituted cycloalkyls" refer to such cyclic groups substituted by an alkyl group of one to six carbon atoms.

The compounds of the formula I posses a significant degree of pharmacological activity. The compounds of the formula I have the properties of antiphlogistics and prostaglandin antagonists. They also inhibit blood platelet aggregation and exhibit analgesic activity. Some derivatives have other favorable effects on the central nervous system.

The pharmacological and toxicological tests show that the compounds of formula I exhibit significant but varying degrees of activity and uniformly low toxicity.

Representative compounds according to this invention were tested for their most significant activities and have been found to be antiphlogistic analgesics and to act as inhibitors of collagen-induced blood platelet aggregation.

The antiphlogistic activity was tested by the rat paw oedema method (Domenju, R: Ann. Univ. Saraviensis 1,317, 1953). The compound were compared with the currently used therapeutic agents Phenylbutazone, aspirin, Indomethacin, Mebron and Amidazophenum.

The test results with the compounds of this invention and the currently acceptable drugs are shown in Table I

TABLE 1

| Substance | Dose mg/kg | Oedema inhibiting effect in % | | |
|---|---|---|---|---|
| | | 1 hour | 2 hours | 24 hours |
| | | after the administration of the substance | | |
| 1,6-dimethyl-3-carboamoyl-4-oxo-1,6,7,S—tetrahydro-4H—pyrido(1,2a)pyrimidine (CH-105) (Examples 1 and 2) | 100 300 | 25 45 | 34 52 | — 8 |
| 1,6-dimethyl-3-(N—tertiary-butyl-carbamoyl)-4-oxo-1,6,7,8-tetrahydro-4H—pyrido(1,2a)pyrimidine (Example 5) | 125 | — | 50 | — |
| 1,6-dimethyl-3-[N—(2-phenyl-ethyl)-carbamoyl]-4-oxo-1,6,7,8-tetrahydro-4H—pyrido (1,2a)pyrimidine (Example 11) | 125 | — | 38 | — |
| 1,6-dimethyl-3-(N—methyl-carbamoyl)-4-oxo-1,6,7,8-tetrahydro-4H—pyrido(1,2a) pyrimidine (Example 7) | 500 | — | 60 | — |
| 1,6-dimethyl-3-(N—phenyl-carbamoyl)-4-oxo-1,6,7,8-tetrahydro-4H—pyrido(1,2a) pyrimidine (Example 6) | 500 | — | 53 | — |
| Mebron | 100 300 | 8 25 | 22 25 | 3 |
| Phenylbutazone | 100 200 | 2 11 | 2 10 | 3 |

According to the latest data in the literature, the prostaglandins play an important role in the inflammatory process (Vane, J. R.: Prostaglandins in the inflammatory response, In.: Inflammation, 1972, N.Y. Academic Press). Thus, it is appropriate to test the effectiveness of a representative compound of the invention in the inflammation response caused by prostaglandin $E_1$ and $E_2$, particularly from the point of view of the vessel wall permeability, which plays an important role in the inflammation.

TABLE 2

| Substance | Dose mg/kg | Oedema inhibition % | | Vessel wall permeability inhibition % | |
|---|---|---|---|---|---|
| | | $PGE_1$ | $PGE_2$ | $PGE_1$ | $PGE_2$ |
| CH-105* | 200 | 30 | 31 | 40 | 35 |
| | 500 | 42 | 45 | 40 | 50 |
| Aspirin | 200 | 41 | 20 | 30 | 25 |
| | 500 | 45 | 54 | 42 | 50 |
| Phenylbutazone | 100 | 35 | 10 | 10 | 5 |
| | 200 | 15 | 28 | 20 | 20 |

*1,6-dimethyl-3-carbamoyl-4-oxo-1,6,7,8-tetrahydro-4H—pyrido-(1,2a)pyrimidine (Examples 1 and 2)

The data of the Table 2 show that CH-105 exhibits an activity of the same range as the known active prostaglandinantagonist, aspirin; as an oedema inhibitor or a vessel wall permeability reducing agent (Vane, J. R. Hospital Practice, 7, 61, 1972).

Favorable antiphlogistic properties were found in tests carried out by the method of Northove. (J. Path. Bect. 85,365, 1963), as shown in Table 3.

TABLE 3

| Substance | Dose mg/kg | Antiphlogistic activity (%) | | |
|---|---|---|---|---|
| | | 1 hour | 2 hours | 24 hours |
| CH-105 | 100 | 40 | 55 | 30 |
| Mebron | 100 | 23 | 23 | 0 |
| Phenylbutazone | 100 | 13 | 20 | 0 |

The significant antiphlogistic activity of CH-105 is advantageously accompanied by analgesic activity. The modified writhing test (Witkin et al: J. Pharm. Exp. Ther. 113, 400 (1961) gave the following results:

TABLE 4

| Substance | $ED_{50}$ mg/kg | Therapeutic Index |
|---|---|---|
| CH-105 | 70 | 14 |
| Mebron | 380 | 4.3 |
| Phenylbutazone | 63 | 5.5 |
| Indomethacin | 2.4 | 12 |

The standard $LD_{50}$ tests as shown in Table 5 demonstrate the favorable toxicity of CH-105 as well as its safety in light of the effective dosages in the tests shown in Tables 1–4.

TABLE 5

| Substance | $LD_{50}$ mg/kg per os | |
|---|---|---|
| | rats | mice |
| CH-105 | 750 | 975 |
| Aspirin | 1600 | 1100 |
| Phenylbutazone | 770 | 350 |

In the course of chronic toxicity tests, CH-105 was not ulcerogenic when administered to one-month old rats in a dose of 50 mg/kg. On the basis of our investigations, CH-105 and the other compounds of formula I show a significant antiphlogistic activity, analgesic activity and have a favorable therapeutic index.

TABLE 6

Thrombocyte Aggregation Inhibiting Effect (in vitro)

| Test compounds | Inhibition of collagen induced thrombocyte aggregation in % CONCENTRATION OF TEST COMPOUND | |
|---|---|---|
| | $1 \times 10^{-4}$ mole | $1 \times 10^{-3}$ mole |
| 1,6-dimethyl-3-carbamoyl-4-oxo-1,6,7,8-tetrahydro-4H—pyrido(1,2a)pyrimidine (CH-105) (Examples 1 and 2) | 90 | 100 |
| 16-dimethyl-3-(N—tertiary, butyl-carbamoyl)-4-oxo-1,6,7,8-tetrahydro-4H—pyrido(1,2a)pyrimidine (Example 5) | 85 | 99 |
| 1,6-dimethyl-3-(N—2-phenethyl-carbamoyl)-4-oxo-1,6,7,8-tetrahydro-4H—pyrido(1,2a)-pyrimidine (Example 11) | 92 | 96 |
| 1,6-dimethyl-3-[N—(3,3-diphenyl-propyl)-carbamoyl]-4-oxo-1,6,7,8-tetrahydro-4H—pyrido(1,2a)pyrimidine (Example 9) | 60 | 70 |
| 1,6-dimethyl-3-(N—phenyl-carbamoyl)-4-oxo-1,6,7,8-tetrahydro-4H—pyrido(1,2a)pyrimidine (Example 6) | 29 | 56 |
| 1,6-dimethyl-3-(N—methyl-carbamoyl)-4-oxo-1,6,7,8-tetrahydro-4H—pyrido(1,2a)pyrimidine (Example 7) | 95 | 100 |

In Table 6 the inhibition of collagen induced thrombocyte aggregation under in vitro conditions is shown. This type of activity has recently been shown to be involved in reducing mortality of patients after a primary heart attack.

The compounds of the formula I can be used as active ingredients in pharmaceutical compositions, admixed with inert, nontoxic liquid, solid or semisolid diluants, vehicles or carriers. The pharmaceutical compositions contain 0.1 to 500 mg of the compounds of formula (I) and are especially useful in the inhibition of thrombocyte aggregation.

Preferred pharmaceutical forms of the present invention are solid forms, such as tablets, capsules, dragees or liquid forms, such as solutions, suspensions or emulsions.

As carriers, the generally used substances, such as talcum, calcium carbonate, magnesium steareate, water, polyethylene glycol may be employed.

A particular feature of the invention is a new method to inhibit thrombocyte aggregation in mammals which comprises the step of administering to said mammal a pharmaceutically effective amount of a compound of the formula (I). Any method of administration conventionally used to inhibit thrombocyte aggregation is contemplated to be within the scope of the invention. Preferred modes of administration include oral and intravenous administration.

It is also preferred to administer the compound of the formula (I) to the mammal in an amount ranging from 0.01 to 250 mg/kg of body weight.

COMPARATIVE TEST RESULTS

Acute toxicity, analgesic and platelet aggregation inhibiting activity of "CH-105" was compared with the same activities of RIMAZOLIUM. RIMAZOLIUM is a commercial product, which is a quaternary salt chemically, but exerts its activity as a tautomeric enamine [Arzneimittel Forschung 21, 717–719 and 719–727 (1971)]. From the formulas given hereinbelow it can be clearly seen that the active form of RIMAZOLIUM shows a close structural relationship with "CH-105".

| Acute toxicity on rats (i.v.) | |
|---|---|
| | $LD_{50}$ (mmoles/kg) |
| CH-105 | 0.96 |
| Rimazolium | 0.61 |
| Analgesic acitvity on rats, hot plate, per os | |
| | $ED_{50}$ (mmoles/kg) |
| CH-105 | 0.41 |
| Rimazolium | 0.62 |
| Analgesic activity on "Writing" test, on mice | |
| | $ED_{50}$ (mmoles/kg) |
| CH-105 | 0.21 |
| Rimazolium | 1.05 |

It has further been found that while CH-105 shows an excellent platelet aggregation inhibiting activity, Rimazolium is practically ineffective under the same conditions.

Rimazolium = 1,6-dimethyl-3-carbethoxy-4-oxo-6,7,8,9-tetrahydrohomopyrimidazol-methylsulfate.

Active form of Rimazolium after in vivo administration is 1,6-dimethyl-3-carbethoxy-4-oxo-1,6,7,8-tetrahydrohomopyrimidazol.

The compositions contain, if desired, some other conventionally used excipients, such as emulsifiers, substances promoting tablet decomposition. The further details of our invention can be found in the following nonlimiting Examples.

EXAMPLE 1

15 g of 1,6-dimethyl-3-carbamoyl-4-oxo-6,7,8,9-tetrahydro-4H-pyrido-(1,2a)pyrimidinium methylsulfate are heated in the mixture of 450 ml of benzene and 50 g of triethylamine and after cooling the mixture is allowed to stand overnight in a refrigerator. The precipitated crystals are filtered. The filtrate is evaporated. The obtained residue is recrystallized from ethanol and thus yellow 1,6-dimethyl-3-carbamoyl-4-oxo-1,6,7,8-tetrahydro-4H-pyrido([1,2a)pyrimidine is obtained. Melting point: 171°–172° C.

Analysis:

calculated: C:59.71%; H:6.83%; N:18.99%; found: C:59.85%; H:6.87%; N:19.03%.

EXAMPLE 2

50 g of 1,6-dimethyl-3-carbamoyl-4-oxo-6,7,8,9-tetrahydro-4H-pyrido(1,2a)pyridinium methylsulfate are dissolved in 150 ml of water and the pH of the solution is adjusted to neutral by adding 13.9 g of solid sodium bicarbonate and from the resulting 1,6-dimethyl-3-carbamoyl-9a-hydroxy-4-oxo-1,6,7,8,9,9a-hexahydro-4H-pyrido(1,2a)pyrimidine 1,6-dimethyl-3-carbamoyl-4-oxo-1,-6,7,8-tetrahydro-4H-pyrido(1,2a)pyrimidine is formed by discharging water and the product is precipitated from the solution in the form of crystals.

After standing for 2 hours at room temperature the crystals are filtered, washed with water and dried. 26.5 g of yellow crystals are obtained, melting point: 165°–171° C. The aqueous filtrate is shaken out with chloroform and the chloroform solution is evaporated and a further 1.8 g of yellow crystals are obtained, melting point: 162°–168° C.

Total yield: 86%. The combined crystalline substance is recrystallized from ethanol and thus the melting point of the resulting 1,6-dimethyl-3-carbamoyl-4-oxo-1,6,7,8-tetrahydro-4H-pyrido(1,2a)pyrimidine is raised to 170°–172° C. There is no decrease in the melting point compared with the product of Example 1.

EXAMPLE 3

15.3 g of 1,6-dimethyl-3-(N-acetyl-carbamoyl)-4-oxo-6,7,8,9-tetrahydro-4H-pyrido(1,2a)pyridinium methylsulfate are dissolved in 50 ml of water. The solution is neutralized with a 5% sodium carbonate solution and thus 1,6-dimethyl-3-(N-acetyl-carbamoyl)-9a-hydroxy-4-oxo-1,6,7,8,9,9a-hexahydro-4H-pyrido(1,2a)pyrimidine is formed which is converted to 1,6-dimethyl-3-(N-acetyl-carbamoyl)-4-oxo-1,6,7,8-tetrahydro-4H-pyrido(1,2a)pyrimidine by discharge of water and it is precipitated from the aqueous solution. The precipitated yellow crystals are filtered, covered with water, and dried. 9.2 g (86%) of the product is obtained, melting point: 182°–184° C. After recrystallization from ethanol the melting point of the resulting 1,6-dimethyl-3-(N-acetyl-carbomoyl)-4-oxo-1,6,7,8-tetrahydro-4H-pyrido(1,2a)pyrimidine is 183°–185° C.

Analysis:
calculated: C: 59.30%; H: 6.51% N: 15.96%; found: C: 59.80%; H: 6.64% N: 15.68%.

EXAMPLE 4

6.38 g of 1-methyl-3-carbamoyl-4-oxo-6,7,8,9-tetrahydro-4H-pyrido(1,2a)pyrimidinium methylsulfate are dissolved in 50 ml of water. The solution is neutralized with solid potassium carbonate and thus 1-methyl-3-carbamoyl-9a-hydroxy-4-oxo-1,6,7,8,9,9a-hexahydro-4H-pyrido(1,2a)pyrimidine is obtained which is transferred under discharge of water to 1-methyl-3-carbamoyl-4-oxo-1,6,7,8-tetrahydro-4H-pyrido(1,2a)-pyrimidine which is precipitated in crystalline form. The yellow crystals are filtered, covered with water and dried. 3.9 g (94%) of yellow substance is obtained. After recrystallization the melting point of the obtained 1-methyl-3-carbanoyl-4-oxo-1,6,7,8-tetrahydro-4H-pyrido(1,2a)-pyrimidine is 241°–242° C.

Analysis:
calculated: C: 57.96%; H: 6.32% N: 20.28%; found: C: 58.09% H: 6.27% N: 20.25%.

EXAMPLE 5

0.89 g (4 mmoles) of 1,6-dimethyl-3-carboxy-4-oxo-1,6,7,8-tetrahydro-4H-pyrido(1,2a)pyrimidine are dissolved in 10 ml of chloroform and 0.62 ml (4.4 mmoles) of chloroformic acid ethyl ester is added dropwise to the mixture under stirring. After stirring for ten minutes a solution of 0.70 g (4.2 mmole) of glycine tertiary butyl ester hydrochloride and 0.58 ml (4.2 mmole) of triethylamine in 10 ml of chloroform are added maintaining the temperature during the addition and for an hour after the addition at $-5°$ to $-10°$ C. The reaction mixture is allowed to stand overnight in the refrigerator, washed three times with 5% sodium bicarbonate and three times with water, dried over sodium sulfate and dried. The residual dark yellow resinous product is dissolved in the mixture of 5 ml of ethyl acetate:pyridine:glacial acetic acid:water=240:20:6:11 and the solution is subjected to chromatography on a Kieselgel 60 column of size 50 cm, diameter: 1.8 cm and of a particle size 0.063–0.125. Eluent solvent:ethyl acetate:pyridine:glacial acetic acid:water=240:20:6:11, flow rate: 30 ml per hour. The solvent, passing through the column is evaporated in vacuo and the residue is held for a while in vacuo of $10^{-2}$ Hgmm, to remove the pyridine acetate of the solvent. 1.00 g of colored amorphous resinous substance is obtained, which is dissolved in 10 ml of ethyl acetate and while still warm, 15 ml of cyclohexane are added. The precipitated crystals are filtered and air-dried the following day. 1.8 g (60%) of 1,6-dimethyl-3-[(N-tert. butoxycarbonyl-methyl)-carbamoyl]-4-oxo-1,6,7,8-tetrahydro-4H-pyrido(1,2a)pyrimidine of a melting point 180°–182° C. is obtained.

Analysis:
calculated: C: 60.88%; H: 7.51%; N: 12.53%; found: C: 61.12%; H: 7.70%; N: 11.94%.

EXAMPLE 6

4.4 g (0.02 moles) of 1,6-dimethyl-3-1,6-dimethyl-3-carboxy-4-oxo-1,6,7,8-tetrahydro-4H-pyrido(1,2a)-pyrimidine and 4.1 ml (0.022 mole) of triethylamine are dissolved in 50 ml of chloroform and the resulting solution is cooled to $-10°$ C. 2.1 ml (0.022 mole) of chloroformic acid ethyl ester is added dropwise to the solution. After stirring for a further ten minutes a solution of 1.95 g (0.022 mole) of aniline in 25 ml of chloroform is added to the mixture, and the temperature is maintained during the addition and after the addition for an hour at $-5°$ C. to $-10°$ C. The reaction mixture is allowed to stand overnight in a refrigerator and the mixture is then shaken out 3-fold with a 5% solution of sodium bicarbonate and then 3 times with water. The chloroform solution is added over sodium sulfate and evaporated in vacuo. 5.7 g (96%) of yellow crystals of a melting point of 180° C. is obtained. After recrystallization twice from ethanol 1,6-dimethyl-3-(N-phenylcarbamoyl)-4-oxo-1,6,7,8-tetrahydro-4H-pyrido(1,2a)pyrimidine is obtained, melting point: 189°–190° C.

Analysis:
calculated: C: 68.67% H: 6.44%; N: 14.13%; found: C: 68.60% H: 6.50%; N: 14.21%.

EXAMPLE 7

4.4 g (0.02 mole) of 1,6-dimethyl-3-carboxy-4-oxo-1,6,7,8-tetrahydro-4H-pyrido(1,2a)pyrimidine and 3.1 ml (0.022 mole) of triethylamine are dissolved in 50 ml of chloroform. THe solution is cooled to $-10°$ C. and 2.1 ml (0.022 mole) of chloroformic acid ethyl ester is added to the solution, whereafter 1.5 g (0.022 mole) of methylamine hydrochloride suspended in 25.0 ml of chloroform and 3.1 ml of triethylamine are also added. The solution is stirred for an hour at a temperature of $-5°$ C. to $-10°$ C. and the mixture is then allowed to stand overnight in a refrigerator. The reaction mixture is then shaken out the following day 3 times with 50 ml of a 5% aqueous solution of sodium carbonate and then with 50 ml of water. The chloroform solution is dried over sodium sulfate and evaporated. 3.9 g (83%) of yellow product is obtained. After recrystallization from ethanol 1,6-dimethyl-3-(N-methyl-carbamoyl)-4-oxo-1,6,7,8-tetrahydro-4H-pyrido(1,2a)pyrimidine is obtained, melting point: 172°–174° C.

Analysis:
calculated: C: b 61.26%; H: 7.28%; N: 17.86; found: C: 61.08; H: 7.40%; N: 17.75%.

EXAMPLE 8

4.4 g (0.02 mole) of 1,6-dimethyl-3-carboxy-4-oxo-1,6,7,8-tetrahydro-4H-pyrido(1,2a)pyrimidine and 3.1 ml of triethylamine are dissolved in 50 ml of chloroform and 2.1 ml (0.022 mole) of chloroform acid ethyl ester and 1.9 g (0.022 mole) of piperidine dissolved in 25 ml of chloroform are added dropwise at −10° C. to the solution. The reaction mixture is stirred for a further hour at −5° C. to −10° C. and it is allowed to stand overnight in a refrigerator.

The following day the chloroform solution is three times shaken out with 50 ml of a 5% solution of sodium bicarbonate and dried over sodium sulfate and evaporated. 5.2 g (90%) of 1,6-dimethyl-4-oxo-3-(piperidyl-carbonyl)-16,7,8-tetrahydro-4H-pyrido(1,2a)pyrimidine is obtained in the form of yellow uncrystallizable oil.

Analysis:
calculated: C: 66.41%; H: 8.01%; N: 14.52%; found: C: 66.58% H: 8.20%; N: 14.47%.

EXAMPLE 9

4.44 g (0.02 mole) of 1,6-dimethyl-3-carboxy-4-oxo-1,6,7,8-tetrahydro-4H-pyrido(1,2a)pyrimidine and 3.1 ml of triethylamine are dissolved in 50 ml of chloroform and 2.1 ml (0.022 mole) of chloroformic acid ethyl ester and 5.26 g (0.022 mole) of diphenylpropylamine dissolved in 25 ml of chloroform are added dropwise at −10° C. to the solution. The reaction mixture is then stirred for 1 hour at a temperature of −5° C. to −10° C. and the mixture is then allowed to stand overnight in a refrigerator. The following day the chloroform solution is shaken out with a 5% sodium bicarbonate solution and with water, dried over sodium sulfate and evaporated. 6.8 g (82%) of yellow crystals are obtained. After recrystallization form ethanol 1,6-dimethyl-3-[N-(3,3-diphenyl-propyl)-carbamoyl]-4-oxo-1,6,7,8-tetrahydro-4H-pyrido(1,2a)pyrimidine of a melting point of 173°–175° C. is obtained.

Analysis:
calculated: C: 75.15%; H: 7.04% N: 10.11%; found: C: 74.92%; H: 6.96% N: 9.84%.

EXAMPLE 10

4.44 g of 1,6-dimethyl-3-carboxy-4-oxo-1,6,7,8-tetrahydro-4H-pyrido(1,2a)pyrimidine and 3.1 ml of triethylamine are dissolved in chloroform at −10° C. and 2.1 ml of chloroformic acid ethyl ester and 1.6 g of tert. butylamine in chloroform are added to the solution. The reaction mixture is stirred at a temperature of −5° C. to −10° C. and it is allowed to stand overnight in a refrigerator. The following day the chloroform solution is shaken out with a 5% sodium bicarbonate solution and then with water, dried over sodium sulfate, filtered and evaporated. 5.3 g (95%) of yellow crystals are obtained. After recrystallization from ethanol 1,6-dimethyl-3-(N-tert-butyl-carbamoyl)-4-oxo-1,6,7,8-tetrahydro-4H-pyrido(1,2a)pyrimidine is obtained, melting point: 179°–181° C.

Analysis:
calculated: C: 64.96%; H: 8.36%; N: 15.15%; found: C: 64.68%; H: 8.32%; N: 15.42%.

EXAMPLE 11

4.44 g of 1,6-dimethyl-3-carboxy-4-oxo-1,6,7,8-tetrahydro-4H-pyrido(1,2a)pyrimidine and 3.1 ml of triethylamine are dissolved in chloroform and 2.1 ml of chloroformic acid ethyl ester and 2.7 g of beta-phenylethylamine are added to the solution at −10° C. The reaction mixture is stirred for an hour at a temperature of −5° C. to −10° C. and then allowed to stand overnight in a refrigerator. The following day the chloroform solution is shaken out with a 5% solution of sodium bicarbonate and then with water, dried over sodium sulfate, filtered and evaporated. 2.1 g of yellow crystals are obtained. After recrystallization from ethanol 1,6-dimethyl-3-[N-(2-phenyl-ethyl)-carbamoyl]-4-oxo-1,6,7,8-tetrahydro-4H-pyrido(1,2a)pyrimidine is obtained, melting point: 141°–143° C.

Analysis:
calculated: C: 70.13%; H: 7.12%; N: 12.91%; found: C: 69.83%; H: 6.96%; N: 12.74%.

EXAMPLE 12

According to the method described in Example 2 but using (−)-1,6-dimethyl-3-carbamoyl-4-oxo-6,7,8,9-tetrahydro-4H-pyrido(1,2a)pyrimidinium-methylsulfate [$(\alpha)_D^{20}$=−59°, (c=2, methanol)] as starting material (+)-1,6-dimethyl-3-carbamoyl-4-oxo-1,6,7,8-tetrahydro-4H-pyrido(1,2a)pyrimidine is obtained, melting point: 171°–173° C. [$(\alpha)_D^{20}$=+71° (c=2, methanol)].

Analysis:
calculated: C: 59.71%; H: 6.83%; N: 18.99%; found: C: 59.69%; H: 6.78%; N: 19.04%.

EXAMPLE 12

According to the method described in Example 2 but using (+)-1,6-dimethyl-2-carbamoyl-4-oxo-6,7,8,9-tetrahydro-4H-pyrido(1,2a)pyrimidine methosulfate [$(\alpha)_D^{20}$=+58.5° (c=2, methanol)] as starting material (−)-1,6-dimethyl-3-carbamoyl-4-oxo-1,6,7,8-tetrahydro-4H-pyrido(1,2a)pyrimidine is obtained [$(\alpha)_D^{20}$=−70°, methanol)].

Analysis:
calculated: C: 59.71%; H: 6.83%; N: 18.99%; found: C: 59.85%; H: 6.90%; N: 18.92%.

EXAMPLE 13

According to the method described in Example 6 but using p-chloroaniline instead of aniline, 1,6-dimethyl-3-[N-(4-chlorophenyl)-carbamoyl]-4-oxo-1,6,7,8-tetrahydro-4H-pyrido(1,2a)pyrimidine (yield: 83%) is obtained, melting point after recrystallization from dimethylformamid: 234°–235° C.

Analysis:
calculated: C: 61.54%; H: 5.47%; N: 12.66%; Cl: 10.68%; found: C: 61.52%; H: 5.80%; N: 12.55%; Cl: 10.79%.

EXAMPLE 14

According to the method described in Example 6 but using p-ethoxy-aniline instead of aniline, 1,6-dimethyl-3-[N-(4-ethoxy-phenyl)-carbamoyl]-4-oxo-1,6,7,8-tetrahydro-4H-pyrido(1,2a)pyrimidine (yield: 63%) is obtained, melting point after recrystallization from dimethylformamid: 192°–194° C.

Analysis: C: 66.84%; H: 6.79%; N: 12.31%; found: C: 66.63%; H: 6.84%; N: 12.25%.

EXAMPLE 15

According to the method described in Example 6 but using m-toluidine instead of aniline, 1,6-dimethyl-3-[N-(3-methyl-phenyl)-carbamoyl]-4-oxo-1,6,7,8-tetrahydro-4H-pyrido(1,2a)pyrimidine (yield: 94%) is obtained, melting point after recrystallization twice from ethanol: 161°–163° C.

Analysis:
calculated: C: 69.43%; H: 6.80%; N: 13.49%; found: C: 69.40%; H: 6.55%; N: 13.60%.

EXAMPLE 16

According to the method described in Example 6 but using p-nitro-aniline instead of aniline, 1,6-dimethyl-3-[N-(4-nitro-phenyl)carbamoyl]-4-oxo-1,6,7,8-tetrahydro-4H-pyrido(1,2a)pyrimidine (yield: 54%) is obtained, melting point after recrystallization from dimethylformamid: 305°–308° C.

Analysis:
calculated: C: 59.64%; H: 5.30%; N: 16.36%; found: C: 60.03%; H: 5.32%; N: 16.48%.

EXAMPLE 17

According to the method described in Example 2 but using 1,7-dimethyl-3-carbamoyl-4-oxo-6,7,8,9-tetrahydro-4H-pyrido(1,2a)-pyridinium methylsulfate as starting material, 1,7-dimethyl-3-carbamoyl-4-oxo-1,6,7,8-tetrahydro-4H-pyrido(1,2a)pyrimidine (yield: 98%) is obtained, melting point after recrystallization from methanol: 232°–234° C.

Analysis:
calculated: C: 59.71%; H: 6.83%; N: 18.99%; found: C: 59.53%; H: 7.19%; N: 18.72%.

EXAMPLE 18

According to the method described in Example 2 but using 1,8-dimethyl-3-carbamoyl-4-oxo-6,7,8,9-tetrahydro-4H-pyrido(1,2a)-pyrimidinium methylsulfate as starting material, 1,8-dimethyl-3-carbamoyl-4-oxo1,6,7,8-tetrahydro-4H-pyrido(1,2a)pyrimidine (yield: 97%) is obtained, melting point after recrystallization from ethanol: 190°–192° C.

Analysis:
calculated: C: 59.71%; H: 6.83%; N: 18.99%; found: C: 59.82%; H: 6.91%; N: 19.03%.

EXAMPLE 19

2 g of 1-ethyl-6-methyl-3-carbamoyl-4-oxo-6,7,8,9-tetrahydro-4H-pyrido(1,2a)pyrimidinium ethylsulfate are dissolved in 20 ml of water and the pH of the solution is adjusted between 7.0 and 8.0 by adding 10% aqueous solution of sodium carbonate and from the resulting 1-ethyl-6-methyl-3-carbamoyl-9a-hydroxy-1,6,7,8,9,9a-hexahydro-4H-pyrido(1,2a)pyrimidino,1-ethyl-6-methyl-3-carbamoyl-4-oxo-1,6,7,8-tetrahydro-4H-pyrido(1,2a)pyrimidine is formed by discharging water and the product is precipitated from the solution in the form of crystals.

0.73 g of 1-ethyl-6-methyl-3a-carbamoyl-4-oxo-1,6,7,8-tetrahydro-4H-pyrido(1,2a)pyrimidine (yield: 56%) are obtained, melting point: 168°–170° C.

Analysis:
calculated: C: 61.26%; H: 7.28%; N: 17.85%; found: C: 61.42%; H: 7.30%; N: 17.91%.

EXAMPLE 20

3.47 g of 1,6-dimethyl-3-(N-methyl-carbamoyl)-4-oxo-6,7,8,9-tetrahydro-4H-pyrido(1,2a)pyrimidinium methylsulfate are dissolved in 30 ml of water and the pH of the solution is adjusted to 7.0 by adding sodium carbonate and from the resulting 1,6-dimethyl-3-(N-methyl-carbamoyl)-9a-hydroxy-4-oxo-1,6,7,8,9,9a-hexahydro-4H-pyrido(1,2a)pyrimidine, 1,6-dimethyl-3-(N-methyl-carbamoyl)-4-oxo-1,6,7,8-tetrahydro-4H-pyrido(1,2a)pyrimidine is formed by discharging water and the product is precipitated from the aqueous solution in the form of crystals. The precipitated crystals are filtered, covered by a little water and dried. 2.3 g of yellow-colored 1,6-dimethyl-3-(N-methyl-carbamoyl)-4-oxo-1,6,7,8-tetrahydro-4H-pyrido(1,2a)pyrimidine (melting point: 174°–175° C.) are obtained. The melting point remains unchanged after recrystallization from ethanol. The product mixed with the product prepared according to Example 7 does not cause a melting point depression.

EXAMPLE 21

| Composition for 5000 × 0.1 g/capsule | |
|---|---|
| (a) 3-carbamoyl-1,6-dimethyl-4-oxo-1,6,7,8-tetrahydro-4H—pyrido(1,2a)pyrimidine (CH-105) | 500 g |
| (b) Potato starch | 115 g |
| (c) Gelatin | 5 g |
| (d) Distilled water | 30 g |
| (e) 2 N hydrochloric acid | 5 g |
| (f) Ethyl alcohol (90%) | 60 g |
| (g) Potato starch | 25 g |
| (h) Talc | 25 g |
| (f) Stearic acid | 5 g |

Method

The powder mixture of components (a) and (b) is moistened with the solution of components (c) to (f) in a suitable kneading-mixing machine, thereafter it is granulated through a 0.3 mm mesh screen and dried at 40° C. The granules thus obtained are regranulated through a 0.15 mm mesh screen. It is admixed with the homogeneous powder mixture of components (g) to (i) and filled into hard gelatin capsules in a filling machine.

Weight of capsule: 0.133 g. The finished capsules are packed in a conventional manner.

EXAMPLE 22

Composition for 5000×0.1 g/tablet, coated pill, dragee
See Example 21.

Method

The granules prepared according to Example 21 are pressed into tablets in a suitable tabletting machine, weight per tablet: 0.133 g. The finished tablets are per se furnished with a film coating, or they are formed into dragee coating with a sugar layer.

EXAMPLE 23

0.4 g tablets of coated pills of prolonged effect.

| Composition for 1000 tablets | |
|---|---|
| CH-105 (active ingredient) | 400 g |
| Crystalline cellulose | 160 g |
| Eudragit lacque | 7 g |
| Potato starch | 35 g |
| Talc | 22 g |
| Magnesium stearate | 6 g |

Method

The mixture of the active ingredient and the crystalline cellulose is granulated by a propanol solution of the Eudragit lacque in a conventional manner. A homogeneous powder mixture of the potato starch, talc and magnesium stearate is admixed with the dried granulated product and is pressed into tablets weighing 0.63 g. The tablets thus obtained may be coated with film- or sugar layer in a manner known per se.

EXAMPLE 24

50 g injection

| Composition for 10,000 ampoules | |
| --- | --- |
| CH-105 | 500 g |
| Sodium chloride | 17 g |
| Sodium pyrosulphite | 3 g |
| Distilled water qs ad | 10.000 cm³ |

Method

In a container suitable for injection purposes the solution of the above composition is prepared in a manner known per se. The nearly isotonic and isohydric solution is filled into 1.1 cm³ ampoules under nitrogen. Sterilization is performed for 30 minutes at 120° C.

EXAMPLE 25

0.15 g suppository

| Composition for 1000 suppositories | |
| --- | --- |
| CH-105 | 150 g |
| Suppository mass | 2,350 g |

Method

The melted suppository mass is dried over about 60 g of anhydrous sodium sulphate and filtered. The active ingredient is homogenized with the warm filtered suppository mass. The suppositories are formed in a suitable machine, and are packed in a conventional manner. As suppository mass cocoa-butter or conventional synthetic suppository substances may be used.

EXAMPLE 26

2% ointment

| Composition for 1000 g of ointment | |
| --- | --- |
| CH-105 | 20 g |
| Methyl cellulose | 50 g |
| Glycerol | 100 g |
| Methyl-p-hydroxy-benzoate | 0.5 g |
| Propyl-p-hydroxy-benzoate | 0.3 g |
| Essence of perfume (secundum artem) | |
| Distilled water qs ad | 1000 g |

Method

The methyl- and propyl-p-hydroxy-benzoates are dissolved in glycerol and homogenized with water-swelled methyl cellulose. The active ingredient and the essence of perfume are dissolved in the water. Water is added to 100 g to finish the product and then it is filled into vials or tubes in a conventional manner.

EXAMPLE 27

| Composition for 1000 combination suppositories | |
| --- | --- |
| CH-105 | 75 g |
| Diethyl barbituric acid | 15 g |
| Rutin | 20 g |
| Nicotinic amide | 25 g |
| Witepsol-H—mass | 1.865 g |

Method

The active ingredient is homogenized with diethyl barbituric acid in a kneading-mixing machine. The rutin and the nicotinic amide are homogenized with dried suppository mass and thereafter the kneaded mixture is homogenized into the dried molten suppository mass. The final mix weighing 2 g is formed into 2 g suppositories in a suitable machine.

EXAMPLE 28

Combination tablet, coated pill or dragees.

| Composition for 1000 tablets, coated pills, dragees | |
| --- | --- |
| CH-105 (active ingredient | 50 g |
| Indomethacin | 10 g |
| Crystalline cellulose | 35 g |
| Polyvinylpyrrolidone | 5 g |
| Colloidal silicic acid | 3 g |
| Talc | 2 g |
| Magnesium stearate | 2 g |

Method

The active ingredient and indomethacin are mixed with crystalline cellulose and polyvinylpyrrolidone and passed through a 0.15 mm mesh screen. Then after incorporating a fine powder mixture of the colloidal silicic acid, talc and magnesium stearate, the product is directly pressed into tablets each weighing 0.107 g.

Remarks

Further to the above Examples, (21–28), other pharmacologically active substances, e.g., alkaloid-type analgesics, dionine, codeine, may also be incorporated into the tablets in a combination with the compounds of formula I.

What is claimed is:

1. 1,6-dimethyl-3-[N(3,3-diphenyl-propyl)carbamoyl]-4-oxo-1,6,7,8-tetrahydro-4H-pyrido(1,2-a)pyrimidine.

2. A method of inhibiting thrombocyte aggregation which comprises the step of administering to a mammal susceptible to thrombocyte aggregation a pharmaceutically effective amount of the compound selected from the group consisting of:
   1,6-dimethyl-3-carbamoyl-4-oxo-1,6,7,8-tetrahydro-4H-pyrido(1,2a)-pyrimidine;
   1,6-dimethyl-3-(N-tertiary-butyl-carbamoyl)-4-oxo-1,6,7,8-tetrahydro-4H-pyrido(1,2-a)pyrimidine;
   1,6-dimethyl-3-(N-2-phenethyl-carbamoyl)-4-oxo-1,6,7,8-tetrahydro-4H-pyrido(1,2-a)pyrimidine;
   1,6-dimethyl-3-[N-(3,3-diphenyl-propyl)-carbamoyl]-4-oxo-1,6,7,8-tetrahydro-4H-pyrido(1,2-a)pyrimidine;
   1,6-dimethyl-3-(N-phenyl-carbamoyl)-4-oxo-1,6,7,8-tetrahydro-4H-pyrido(1,2-a)pyrimidine; and
   1,6-dimethyl-3-(N-methyl-carbamoyl)-4-oxo-1,6,7,8-tetrahydro-4H-pyrido(1,2-a)pyrimidine.

* * * * *